United States Patent
Procyshyn et al.

(10) Patent No.: US 10,261,940 B2
(45) Date of Patent: Apr. 16, 2019

(54) ROBOTIC FILLING SYSTEMS AND METHODS

(71) Applicant: Vanrx Pharmasystems Inc., Burnaby (CA)

(72) Inventors: Christopher Procyshyn, Surrey (CA); Ross M. Gold, North Vancouver (CA)

(73) Assignee: VANRX PHARMASYSTEMS, INC., Burnaby (CA)

( * ) Notice: Subject to any disclaimer, the term of this patent is extended or adjusted under 35 U.S.C. 154(b) by 0 days.

(21) Appl. No.: 15/680,114

(22) Filed: Aug. 17, 2017

(65) Prior Publication Data

US 2018/0189275 A1    Jul. 5, 2018

Related U.S. Application Data

(60) Continuation of application No. 13/774,408, filed on Feb. 22, 2013, now Pat. No. 8,651,368, which is a
(Continued)

(51) Int. Cl.

| | |
|---|---|
| *G06F 16/00* | (2019.01) |
| *B65B 3/00* | (2006.01) |
| *B65B 55/02* | (2006.01) |
| *B65B 7/28* | (2006.01) |
| *G01N 35/00* | (2006.01) |

(Continued)

(52) U.S. Cl.
CPC .............. *G06F 16/00* (2019.01); *B25J 21/00* (2013.01); *B65B 3/003* (2013.01); *B65B 7/2807* (2013.01); *B65B 7/2821* (2013.01); *B65B 55/027* (2013.01); *G06F 1/1626* (2013.01); *G06F 1/1632* (2013.01); *G06F 1/1696* (2013.01); *H04M 1/04* (2013.01);
(Continued)

(58) Field of Classification Search
CPC .............. H04M 1/04; H04M 1/72527; H04M 1/72575; G06F 1/30; G06F 1/1626; G06F 1/1632; G06F 1/1696; B65B 1/00; B65B 3/00; B65B 5/00

See application file for complete search history.

(56) References Cited

U.S. PATENT DOCUMENTS

| | | |
|---|---|---|
| 4,146,924 A | 3/1979 | Birk et al. |
| 4,402,053 A | 8/1983 | Kelley |

(Continued)

FOREIGN PATENT DOCUMENTS

| | | | |
|---|---|---|---|
| JP | 2002068103 A | * | 3/2002 |
| JP | 2002068103 A2 | | 3/2002 |
| WO | 2009111019 A1 | | 9/2009 |

OTHER PUBLICATIONS

International Application Serial No. PCT/US2009/01368, International Search Report dated Apr. 30, 2009, 5 pages.
(Continued)

*Primary Examiner* — Laura A Gudorf
(74) *Attorney, Agent, or Firm* — Kevin R. Erdman; Brannon Sowers & Cracraft PC

(57) ABSTRACT

Systems and methods are disclosed, which permit filling containers with a product. A filling arm is disposed within a chamber and an optical sensor is configured to sense openings of the containers within the chamber. Locations of the sensed openings are used to guide the filling arm to fill the containers with a product.

26 Claims, 7 Drawing Sheets

Related U.S. Application Data division of application No. 12/393,183, filed on Feb. 26, 2009, now abandoned.

(60) Provisional application No. 61/033,682, filed on Mar. 4, 2008.

(51) Int. Cl.
| | |
|---|---|
| *B25J 21/00* | (2006.01) |
| *G06F 1/16* | (2006.01) |
| *H04M 1/04* | (2006.01) |
| *H04M 1/725* | (2006.01) |
| *G01N 35/10* | (2006.01) |

(52) U.S. Cl.
CPC .... *H04M 1/72527* (2013.01); *G01N 35/0099* (2013.01); *G01N 35/10* (2013.01); *H04M 1/72575* (2013.01)

(56) References Cited

U.S. PATENT DOCUMENTS

| | | |
|---|---|---|
| 4,494,583 A | 1/1985 | Reeves, Jr. et al. |
| 4,572,253 A | 2/1986 | Farmer et al. |
| 4,645,993 A | 2/1987 | Naito et al. |
| 4,798,232 A | 1/1989 | Stembridge et al. |
| 4,813,845 A | 3/1989 | Swain |
| 4,881,581 A | 11/1989 | Hollerback |
| 4,886,412 A | 12/1989 | Wooding et al. |
| 4,917,155 A | 4/1990 | Koblasz et al. |
| 4,972,883 A | 11/1990 | Hassell et al. |
| 4,985,846 A | 1/1991 | Fallon |
| 5,059,789 A | 10/1991 | Salcudean |
| 5,305,581 A | 4/1994 | Reeves, Jr. et al. |
| 5,316,733 A | 5/1994 | Rune |
| 5,491,333 A | 2/1996 | Skell et al. |
| 5,628,665 A | 5/1997 | Lang |
| 5,943,476 A | 8/1999 | Dougherty et al. |
| 5,947,951 A | 9/1999 | Ortiz et al. |
| 5,965,447 A | 10/1999 | Sekiyama et al. |
| 6,053,219 A | 4/2000 | Seiver |
| 6,227,265 B1 | 5/2001 | Skell et al. |
| 6,256,964 B1 | 7/2001 | Drevfors |
| 6,431,407 B1 | 8/2002 | Hogan et al. |
| 6,836,692 B2 | 12/2004 | Leavitt |
| 6,857,250 B1 | 2/2005 | Taylor |
| 6,863,092 B2 | 3/2005 | Seiver et al. |
| RE38,747 E | 6/2005 | Jagger |
| 7,013,932 B2 | 3/2006 | Berghoff et al. |
| 7,322,170 B2 | 1/2008 | Tomalesky |
| 7,474,939 B2 | 1/2009 | Oda |
| 7,559,737 B2 | 7/2009 | Ray |
| 7,896,602 B2 | 3/2011 | Rebstock |
| 8,226,073 B2 | 7/2012 | Li |
| 8,458,992 B2 | 6/2013 | Zanini |
| 8,777,540 B2 | 7/2014 | Rebstock |
| 2001/0050116 A1 | 12/2001 | Skell et al. |
| 2003/0051326 A1* | 3/2003 | Lawson ............ B23P 19/04 29/407.01 |
| 2003/0056466 A1 | 3/2003 | Muneyasu |
| 2003/0164200 A1 | 9/2003 | Czeranna et al. |
| 2004/0084340 A1 | 5/2004 | Morelle et al. |
| 2004/0089373 A1 | 5/2004 | Seiver et al. |
| 2005/0132822 A1 | 6/2005 | Massaro |
| 2005/0194059 A1* | 9/2005 | Py .................. B65B 3/003 141/18 |
| 2005/0229548 A1 | 10/2005 | Hooper |
| 2006/0048844 A1 | 3/2006 | Merrill et al. |
| 2006/0151048 A1 | 7/2006 | Tochon-Danguy et al. |
| 2006/0259195 A1* | 11/2006 | Eliuk .................. A61J 1/20 700/245 |
| 2007/0069087 A1 | 3/2007 | Mumm |
| 2007/0267095 A1* | 11/2007 | Wadium .............. B65B 1/18 141/140 |
| 2008/0006675 A1 | 1/2008 | Kraus |
| 2008/0083371 A1 | 4/2008 | Clifford et al. |
| 2008/0251473 A1 | 10/2008 | Rebstock et al. |
| 2012/0165171 A1 | 6/2012 | Chiu et al. |
| 2012/0267055 A1 | 10/2012 | Rogalla et al. |

OTHER PUBLICATIONS

International Application Serial No. PCT/US2009/01368, International Written Opinion dated Apr. 30, 2009, 8 pages.
European Search Opinion, dated Feb. 26, 2016.
Supplemental European Search Report, dated Feb. 26, 2016.
European Amendment, dated Sep. 21, 2016.
USPTO, Non-Final Office Action for U.S. Appl. No. 12/393,183 dated Apr. 6, 2011.
USPTO, Response to Non-Final Office Action for U.S. Appl. No. 12/393,183, dated Sep. 6, 2011.
USPTO, Final Office Action for U.S. Appl. No. 12/393,183 dated Oct. 6, 2011.
USPTO, Response to Final Office Action for U.S. Appl. No. 12/393,183, dated Apr. 13, 2012.
USPTO, Non-Final Office Action for U.S. Appl. No. 12/393,183 dated Sep. 13, 2013.
USPTO, Response to Non-Final Office Action for U.S. Appl. No. 12/393,183, dated Mar. 13, 2014.
USPTO, Final Office Action dated Mar. 27, 2014, U.S. Appl. No. 12/393,183.
USPTO, Final Office Action for U.S. Appl. No. 13/744,408 dated May 11, 2016.
USPTO, Response to Final Office Action for U.S. Appl. No. 13/744,408, dated Nov. 14, 2016.

\* cited by examiner

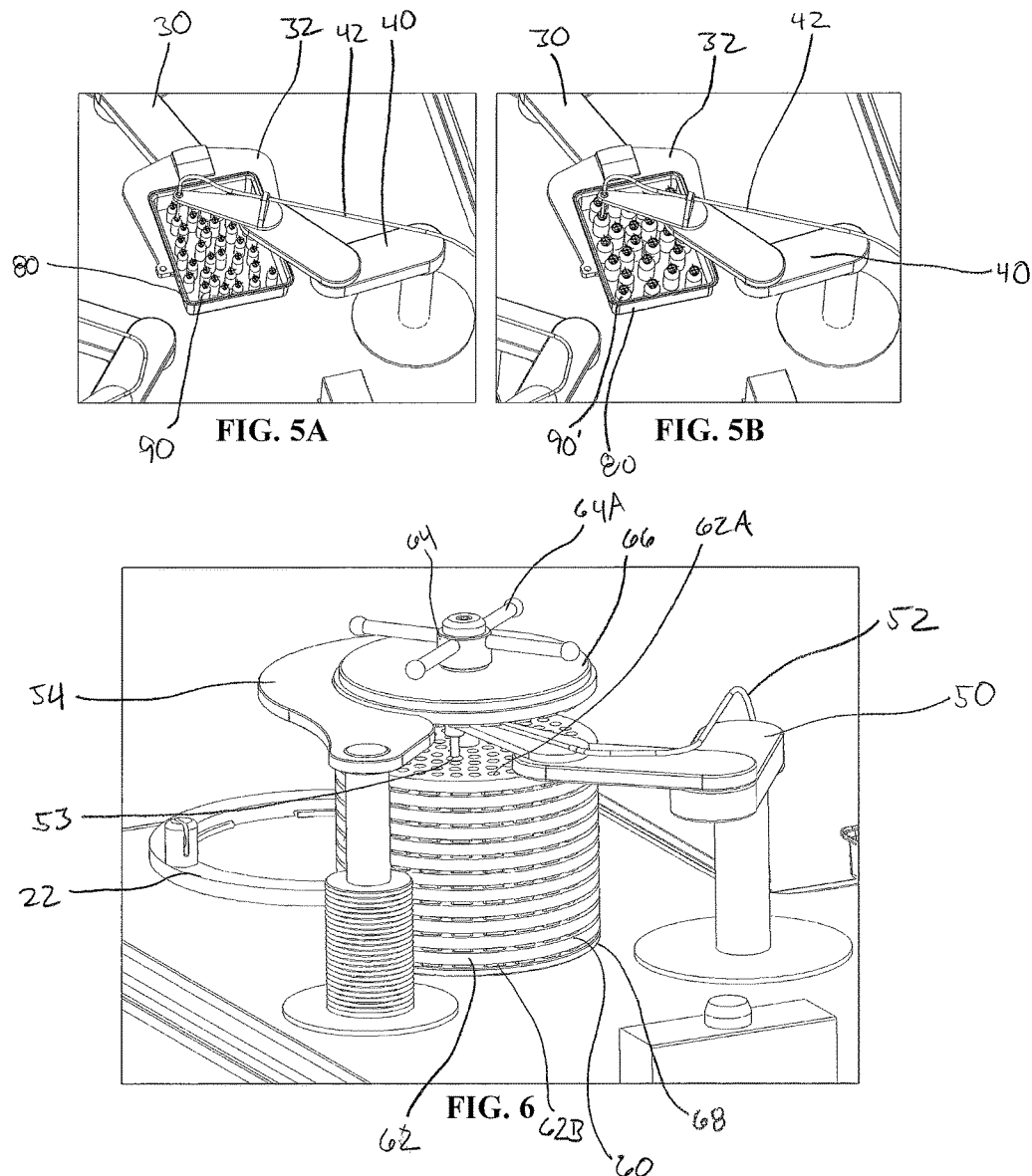

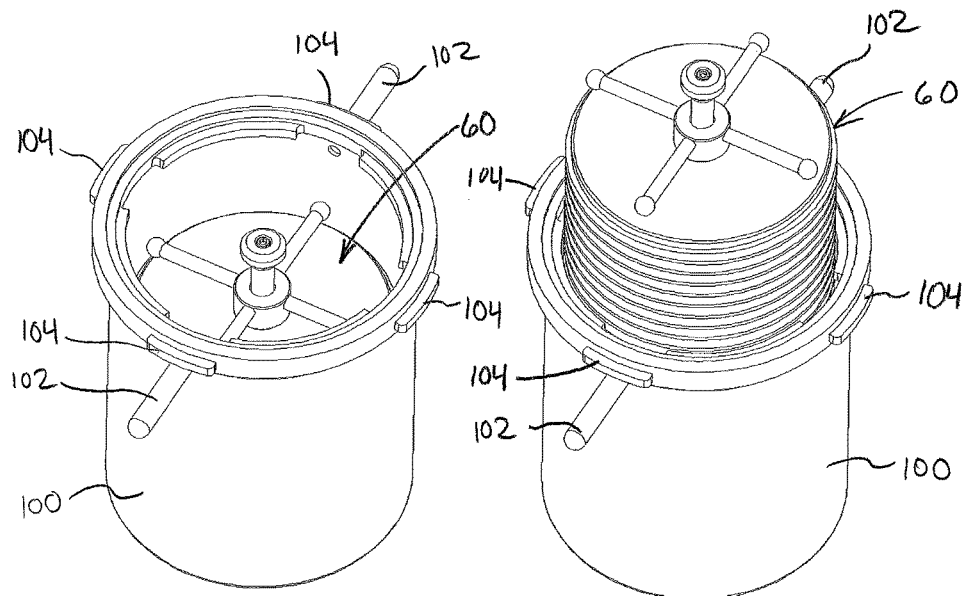
FIG. 10A   FIG. 10B
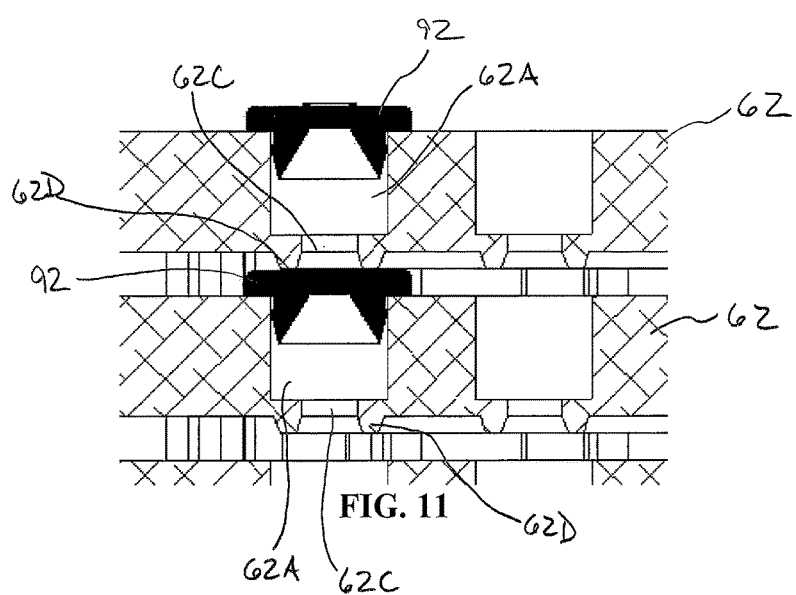
FIG. 11

ROBOTIC FILLING SYSTEMS AND METHODS

RELATED APPLICATION

This application is a continuation of U.S. patent application Ser. No. 13/744,408 filed Jan. 17, 2013, which is a divisional of U.S. patent application Ser. No. 12/393,183 filed Feb. 26, 2009 and claims the benefit of U.S. Provisional Patent Application Ser. No. 61/033,682, filed Mar. 4, 2008, which applications are all incorporated herein by reference in their entirety.

BACKGROUND

By its very nature, the production of sterile pharmaceuticals by humans can be problematic. Humans can be a large source of microbial contamination. Also, with increased potencies, some drugs can be hazardous in occupational exposure. For at least these reasons, robotics can be used in dosage manufacturing to limit human contact. Isolator technology, which provides a solid barrier between a process and humans, can also be used in dosage manufacturing to limit human contact.

To enable sterile processing, isolator technology adapted various vapor and gas sterilization systems, bringing about an advance in aseptic processing. Articulated cleanroom robots have been employed which utilize internal negative pressure with an exhaust to generate cleanroom capability. With the chemical sterilization and handling of potent drugs within the isolator, an internal negative pressure cleanroom with an exhaust is not feasible, due largely to the leakage potential.

Sterile manufacturing is performed by various companies, often outsourced companies, including small cleanroom facilities and large pharmaceutical facilities. Often, small cleanroom facilities are not optimally equipped for pharmaceutical filling operations, which can lead to a lower quality product and higher risk for the outsourcing company. Conversely, large pharmaceutical facilities with high-speed lines generally can produce a higher quality product, but have relatively limited flexibility with respect to batch size, variations of product, and timing.

OVERVIEW

The present inventors have recognized, among other things, that there exists a need for a filling system that allows for increased flexibility while, at the same time, allowing for increased quality of product.

In some embodiments, systems permit filling containers with a product. A filling arm is disposed within the chamber. An optical sensor is configured to sense openings of the containers within the chamber. Locations of the sensed openings are used to guide the filling arm to fill the containers with a product.

In some embodiments, methods permit filling containers with a product. Openings of the containers are optically sensed. The containers are filled with the product using locations of the sensed openings of the containers.

In some embodiments, systems permit filling containers with a product. A chamber is configured to maintain an environmental condition. A filling arm is disposed within the chamber. A sensor is configured to sense openings of the containers within the chamber. Locations of the sensed openings are used to guide the filling arm to fill the containers with a product.

BRIEF DESCRIPTION OF THE DRAWINGS

The drawings illustrate generally, by way of example, but not by way of limitation, various embodiments discussed in the present document.

FIGS. 5A and 5B are perspective views of a filling arm of a robotic filling system according to some embodiments of the disclosed subject matter, the filling arm filling containers.

FIG. 6 is a perspective view of a stopper disc stack of a robotic filling system according to some embodiments of the disclosed subject matter.

FIGS. 10A and 10B are perspective views of a stopper disc stack of a robotic filling system according to some embodiments of the disclosed subject matter, the stopper disc stack within a transfer container.

FIG. 11 is a cross-sectional view of stoppers held within a portion of a stopper disc stack of a robotic filling system according to some embodiments of the disclosed subject matter.

DESCRIPTION

The present inventors have recognized, among other things, that there exists a need for a filling system that allows for increased flexibility while, at the same time, allowing for increased quality of product. The present inventors have developed systems and methods for filling containers with products, which, as described in more detail below, allow for increased flexibility and increased quality.

Figure 1:
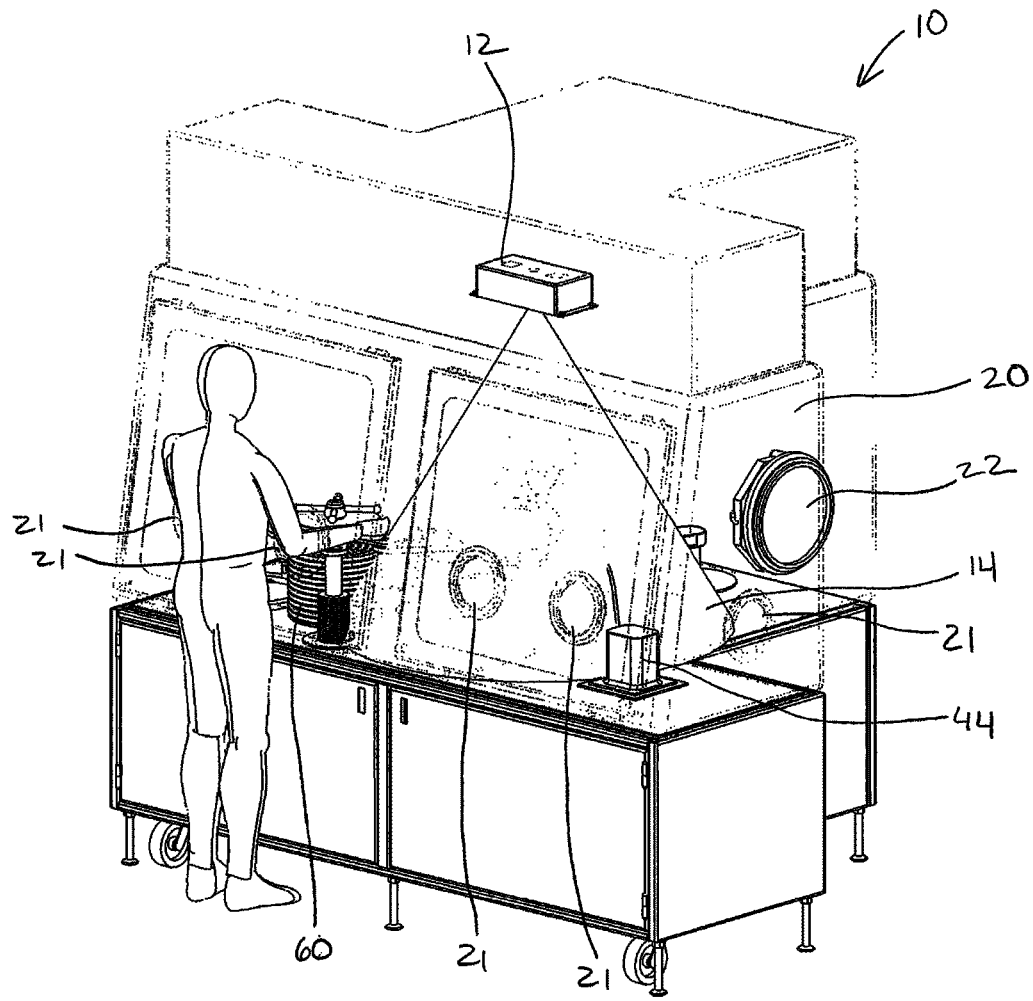
FIG. 1 is a perspective view of a robotic filling system according to some embodiments of the disclosed subject matter.
Figure 2:
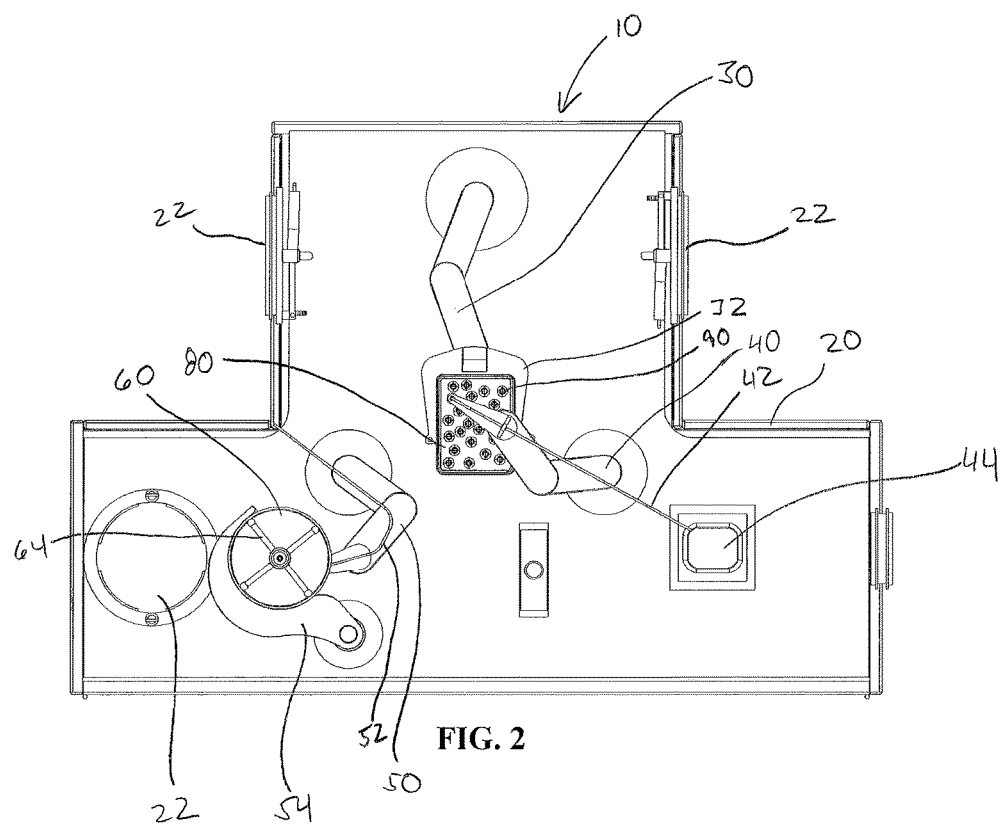
FIG. 2 is a top cutaway view of a robotic filling system according to some embodiments of the disclosed subject matter.

Referring to FIGS. 1 and 2, in an example, a filling system 10 is configured to fill containers 90 with a product. In one example, the product is a liquid product. In another example, the product is a pharmaceutical product. In another example, the product is potentially toxic or otherwise harmful. As will be described in more detail below, the filling system 10 can be configured to locate, target, and fill randomly placed containers 90 within a tray 80 or nest, without the need for mechanical container handling parts, or other change parts for filling equipment. Many types of containers 90 are contemplated herein, including, but not limited to vials, syringes, bottles, beakers, test tubes, etc.

In one example, the filling system 10 includes a chamber 20 configured to maintain desired environmental conditions. In one example, the chamber 20 is an isolator chamber capable of maintaining an aseptic environment within the chamber 20. The chamber 20, in one example, includes one or more ports 22 for access to the interior of the chamber 20. In one example, the port 22 is a rapid transfer port to allow for aseptic transfer of articles from a container, such as a transfer isolator, to the chamber 20. Briefly, in one example, the rapid transfer port 22 can be configured to mate with a door of the container such that the unsterilized exterior surfaces mate against and attach to each other before opening, such that, when the port 22 and door combination is opened, the unsterilized exterior surfaces of the door and port 22 are contained against each other, thereby limiting contamination of the interior environments of the container and the chamber 20. The filling system 10 can include proximity sensors or other such devices to sense when a container or transfer isolator is engaged with the port 22. In this way, opening of the port 22 while not engaged with a container or transfer isolator, and, in turn, contamination of the interior environmental conditions, can be guarded against. The ports 22 are described in more detail below.

In one example, the chamber 20 includes one or more glove holes 21 disposed in the walls of the chamber 20. The glove holes 21 can be used to manually manipulate objects within the chamber 20 without opening the chamber 20 or otherwise compromising the environmental conditions within the chamber 20.

In one example, a filling arm 40 is disposed within the chamber 20. The filling arm 40, in one example, is a robotic arm. The filling arm 40 includes filling tubing 42 extending from a pump unit 44 to a point at an end of the filling arm 40. In one example, an outlet of the filling tube 42 includes a valve, filling needle, or other flow controlling device to control discharge of the product from the filling tubing 42. In one example, the filling tubing 42 extends from the reservoir and through the pump 44. The pump 44 is configured to selectively urge the product from a reservoir, through the filling tubing 42, and into the containers 90. In one example, the pump 44 is a peristaltic pump, such as a rotary or a linear peristaltic pump. As will be described in more detail below, the filling arm 40 positions the outlet of the filling tubing 42 over each container 90 to allow filling of the containers 90 with product.

The filling system 10, in some examples, includes a sensor 12 for sensing the containers 90 within the chamber 20. In one example, the sensor 12 senses openings of the containers 90. In other examples, the sensor 12 is an optical sensor, a camera system, or a laser system. The sensor 12, in one example, is mounted at a top surface of the chamber 20 and is positioned to sense an area within the chamber 20, as portrayed by a sensing cone 14. For instance, the optical sensor 12 can be configured to locate containers 90 within the sensing cone 14 and target centers of the openings of the containers 90. The locations of the sensed openings of the containers 90 are used to guide the filling arm 40 to fill the containers 90 with product. In one example, the targeted centers are used by a controller for controlling the filling arm 40. In one example, the optical sensor 12 is configured to perform a pre-fill inspection of containers 90 to determine if any containers are defective or otherwise unfit for filling. If such a defective container is found, the container can be ignored during the filling process so as to reduce waste of product and limit potential leakage.

In one example, a holding arm 30 is disposed within the chamber 20 for transporting and holding the containers 90 within the chamber 20. The chamber 20, in one example, includes a stoppering arm 50 configured to stopper or otherwise close the openings of the containers 90. These aspects of the filling system 10 are discussed in greater detail below.

In some examples, one or more of the holding arm 30, filling arm 40, and stoppering arm 50 are servo-driven robotic arms. In other examples, the arms 30, 40, 50 can be of differing configurations, provided they are capable of functioning in the manners described herein.

Referring now to FIGS. 3, 4, 5A, and 5B, the holding arm 30 can be used to perform multiple tasks, including, for instance, opening doors 28 of ports 22 and transporting and holding containers 90. The holding arm 30, in one example, includes a generally U-shaped end effect tool 32. In one example, the end effect tool 32 includes a hole 32A on one "leg" of the U-shaped tool 32, a hook 32B on the other "leg" of the U-shaped tool 32, and a shoulder 32C around an interior edge of the tool 32. In other examples, the end effect tool can include different configurations depending upon the interactions and tasks required of the holding tool.

The hole 32A and the hook 32B are configured to allow the holding arm 30 to open and close the ports 22 to allow for containers 90 to enter and exit the chamber 20. For instance, a transfer isolator or other such container can be used to transfer sterilized containers into the chamber 20. In one example, once a transfer isolator or other container is attached to the port 22, as signaled by the proximity sensor or other such device, the controller can control the holding arm 30 to open the port 22.

Figure 3:
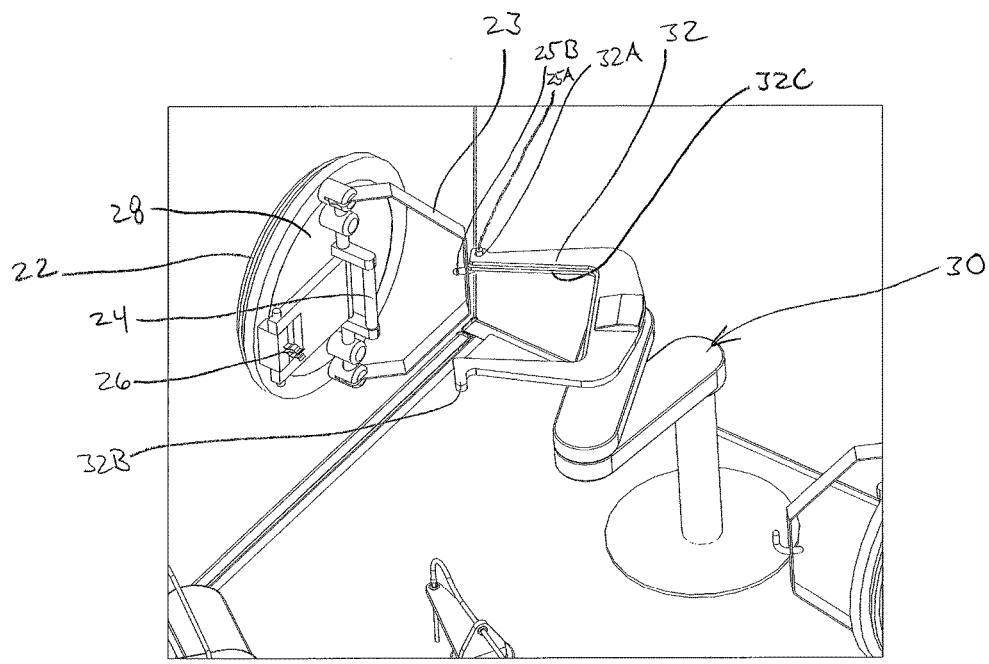
FIG. 3 is a perspective view of a robotic arm and a port of a robotic filling system according to some embodiments of the disclosed subject matter.
Figure 4:
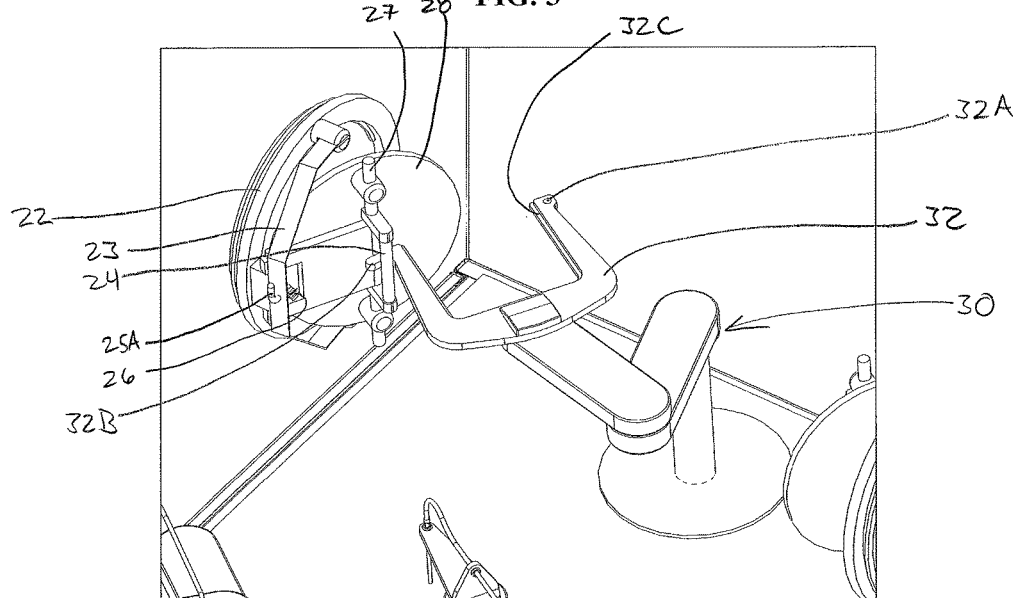
FIG. 4 is a perspective view of a robotic arm and a port of a robotic filling system according to some embodiments of the disclosed subject matter.

As shown in FIG. 3, the hole 32A is configured to selectively engage with a post 25A of a clamp handle 23 to allow the holding arm 30 to manipulate the clamp handle 23. Pivoting of the clamp handle 23 to an unlocked position (FIG. 4) releases posts 27 of the door 28 to allow the door 28 to be opened. In one example, the clamp handle 23 includes a pin 25B, which is engageable within a clasp 26 to maintain the clamp handle 23 in the unlocked position.

Once the clamp handle 23 is in the unlocked position, the hook 32B of the holding arm 30 can be used to interact with a handle 24 of the door 28 to pivot the door 28 to an open position. As described above, the door of the container or transfer isolator can be engaged with the door 28 to open with the door 28, thereby allowing the holding arm 30 to access the interior of the transfer isolator or container, while generally maintaining the desired environmental conditions within the chamber 20. In one example, the containers 90 are held on a tray 80 or other such holder configured to allow the holding arm 30 to pick up the tray 80 using the shoulder 32C. In this example, the tool 32 is extended into the transfer isolator or container and positioned such that the shoulder 32C of the tool 32 abuts a bottom side of a rim of the tray 80. The holding arm 30 can then pick up the tray 80 to transport it into the chamber 20. Once the tray 80 is transported within the chamber 20, in one example, the port 22 can be closed by the holding arm 30 in a reverse manner to that described above to open the port 22. In another example, the port 22 can remain open, for instance, to replace the tray 80 of containers 90 once the containers 90 have been filled. In another example, once the containers 90 have been filled, the holding arm 30 can be used to open a port 22, as described above, and to place the tray 80 of filled containers 90 within a transfer isolator or other container engaged thereto for removal of the filled containers 90 from within the chamber 20.

Referring to FIGS. 2, 5A, and 5B, in one example, once the tray 80 is received by the tool 32, the holding arm 30 transports the tray 80 to a filling position within the chamber 20. In one example, the filling position is a location within the chamber 20 that is within the sensing cone 14 and within reach of the filling arm 40. Once the tray 80 of containers 90 is in the filling position, the sensor 12, for instance an optical sensor, can be activated to locate the containers 90 and target the openings of the containers 90. In one example, pattern recognition software is employed to analyze data from the sensor 12 to identify suitable filling locations corresponding to the openings of the containers 90 within the chamber 20. In this way, the containers 90 in various positions on the tray 80, including random positions, can be located and targeted by the sensor 12 and pattern recognition software and need not be positioned with any particular pattern or spacing. Additionally, such locating and targeting can be performed regardless of the size of the containers 90. In one example, as shown in FIG. 5A, containers 90 of a first size are located and targeted. In another example, as shown in FIG. 5B, containers 90' of a second size are located and targeted. The pattern recognition software, in one example, is implemented in the controller of the filling system 10. In another example, the pattern recognition software is implemented in a computer or control module different from the controller of the filling system 10.

In one example, the positions of the containers 90 are used to control the filling arm 40 to travel to the predetermined filling locations and dispense the product into the containers 90, 90'. In one example, the positions of the containers 90 are also used to control the stoppering arm 50, which picks up a closure for the container 90, 90' and places it into the opening of the container 90, 90', as described in more detail below.

Figure 7:
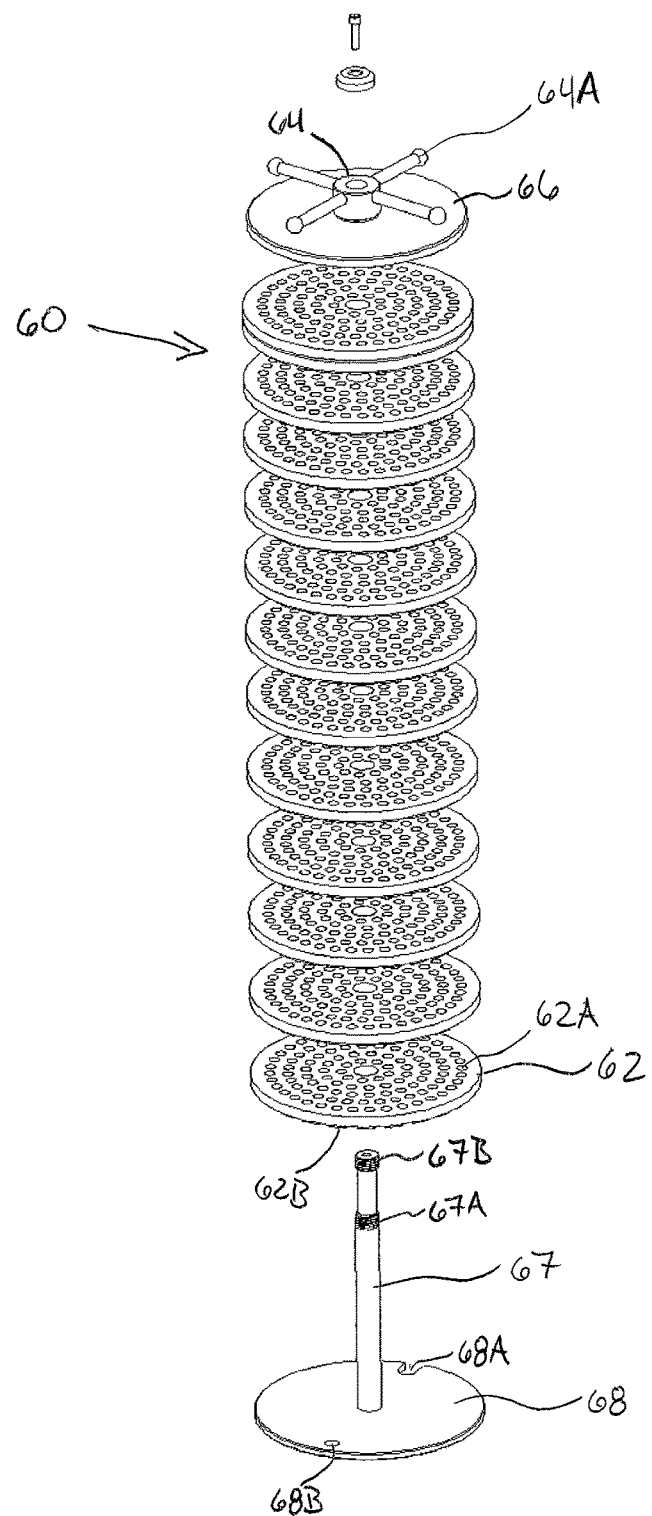
FIG. 7 is an exploded view of a stopper disc stack of a robotic filling system according to some embodiments of the disclosed subject matter.

Referring to FIGS. 6, 7, and 11, in one example, the stoppering arm 50 is configured to pick up and place stoppers 92 or other closures in the openings of the containers 90. Closures contemplated for use with the filling system 10 include lyophilization stoppers, serum stoppers, syringe stoppers, and the like. In some examples, the stoppering arm 50 includes a gripping implement 53 at the end thereof. In one example, the stoppering arm 50 includes tubing 52 extending from a vacuum source to an end of the stoppering arm 50. In one example, the tubing 52 connects to the gripping implement 53, the gripping implement 53 being actuated by pulling of a vacuum through the tubing 52. In another example, the gripping implement includes mechanical grasping members, such as mechanically-actuated fingers or other such mechanical grasping mechanisms.

In one example, the stoppering arm 50 picks up stoppers 92 from a stopper disc stack 60. In some examples, the stopper disc stack 60 includes one or more stopper discs 62 stacked on a spindle 67 sandwiched between a top plate 66 and a bottom plate 68. The discs 68 are axially slidable along the spindle 67. In one example, a top nut 64 is disposed on the spindle 67 and acts to retain the top plate 66 on the spindle 67. In one example, the top nut 64 is integrally attached to the top plate 66. In one example, the top nut 64 includes one of more handles 64A to allow for manual manipulation of the top nut 64. In one example, the spindle 67 includes first threads 67A, which engage the top nut 64 in a first, closed position (see FIG. 8) where the top plate 66 is stacked on top of the uppermost disc 62 and second threads 67B, which engage the top nut 64 in a second, open position (see FIG. 9) to allow access to the stoppers or other closures within the stopper disc stack 60.

In one example, the discs 62 are circular, although other shapes of discs are contemplated. In one example, each of the discs 62 includes a plurality of recesses 62A configured to hold stoppers 92 or other closures therein. As shown in FIG. 11, the recesses 62A, in one example, do not extend through the entire disc 62 to allow for stoppers 92 to be seated within the recesses 62A but not fall through the disc 62. In a further example, a hole 62C having a width smaller than the width of the recess 62A is disposed through the remainder of the disc 62 at the bottom of the recess 62A. The hole 62C allows for penetration of sterilants, such as steam, ethylene oxide, and hydrogen peroxide vapor. Each of the discs 62 can include one or more feet 62B extending from a bottom surface of the disc 62. The feet 62B abut the disc 62 below to create spacing between adjacent discs 62 in the stopper disc stack 60. In one example, each of the discs 62 can include indentations in a top surface of the disc 62 which correspond to and accept the feet 62B.

The recesses 62A of stopper disc stack 60 provide positions to hold stoppers 92 or closures in place during movement and processing. The discs 62, in some examples, can be made of polymeric materials, such as PTFE, HDPE, LDPE, polyetherimide, polysulphone, polybenzimidazole, polyamide-imide, polyetherimide, polyimide, polyarylether ketones, or polythermide, or metals, such as stainless steel, titanium, aluminum, or hastelloy. Also, in further examples, the metals can be coated or otherwise treated to provide a non-stick or decreased-stick surface, using, for instance, a hard annodization process or other such treatment or coating processes. In one example, as shown in FIG. 11, each disc 62 is machined or otherwise formed on a lower surface to produce a convoluted surface 62D to maintain contact with stoppers 92 or other closures held by the disc 62 below. In one example, such contact in maintained to a minimum to enable penetration of sterilants such as steam, ethylene oxide, and hydrogen peroxide vapor. In one example, the stopper disc stack 60 is compatible with sterilization by radiation, such as electron beam irradiation and gamma irradiation. In one example, the discs 62 cooperate to effectively surround the stoppers 92 or other closures between the sandwiched discs 62 to allow for containment of the stoppers 92 or other closures during multi-axis movement of the stopper disc stack 60.

The stopper disc stack 60, in some examples, is disposed within the chamber 20 during container filling to provide stoppers 92 or other closures for closing the containers 90 after filling. In one example, the stopper disc stack 60 is placed on a rotating turntable within the chamber 20. The stopper disc stack 60 can include engagement features, such as, for instance, a notch 68A and a hole 68B in the bottom plate 68, to engage the stopper disc stack 60 with the turntable so as to rotate therewith, and to ensure that the stopper disc stack 60 is able to be indexed for stopper 92 removal. It should be understood that the above-described engagement features are not intended to be limiting and that other engagement features are contemplated herein. In this way, rotation of the turntable causes rotation of the stopper disc stack 60. In one example, each of the discs 62 of the stopper disc stack 60 are able to rotate with the turntable due to the interaction of the feet 62B on the bottom side of each of the discs 62 with the indentations in the top side of each of the adjacent discs 62.

Referring now to FIGS. 1, 2, 10A, and 10B, the stopper disc stack 60 can be introduced within the chamber 20 manually by a user. In some examples, the stopper disc stack 60 can be introduced within the chamber 20 without disrupting the environmental condition within the chamber 20. The stopper disc stack 60 can be transported, for instance, from an autoclave or from a storage location, to the filling system 10 using a transfer isolator 100 or other container. As described above, the transfer isolator 100 or other container can be engaged with a port 22 in the chamber 20. In one example, the transfer isolator 100 or other container is engaged with the horizontally-oriented port 22 disposed in a floor of the chamber 20. In one example, the transfer isolator 100 or other container includes handles 102 to facilitate handling of the transfer isolator 100 or other container and engagement of the transfer isolator 100 or other container with the port 22, for instance. In one example, the transfer isolator 100 or other container includes tabs 104 or other engagement features configured to interact with corresponding tabs or other engagement features associated with the port 22, such that rotation of the transfer isolator 100 or other container with respect to the port 22 engages the tabs 104 of the transfer isolator 100 or other container with the engagement features of the port 22 to engage the transfer isolator 100 or other container with the port 22. Once the transfer isolator 100 or other container is engaged with the port 22, the user can manually open the door of the port 22 using the glove holes 21 (FIG. 1), grasp the stopper disc stack 60 using the handles 64A of the top nut 64, lift the stopper disc stack 60 from the transfer isolator or other container, and place the stopper disc stack 60 on the turntable within the chamber 20. Although introduction of the stopper disc stack 60 is described as a manual process, it is contemplated herein that the process can be automated.

Figure 8:
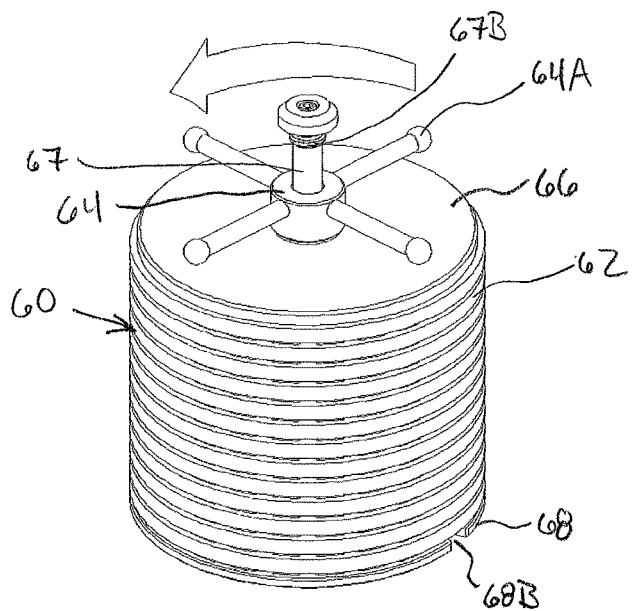
FIG. 8 is a perspective view of a stopper disc stack of a robotic filling system according to some embodiments of the disclosed subject matter.
Figure 9:
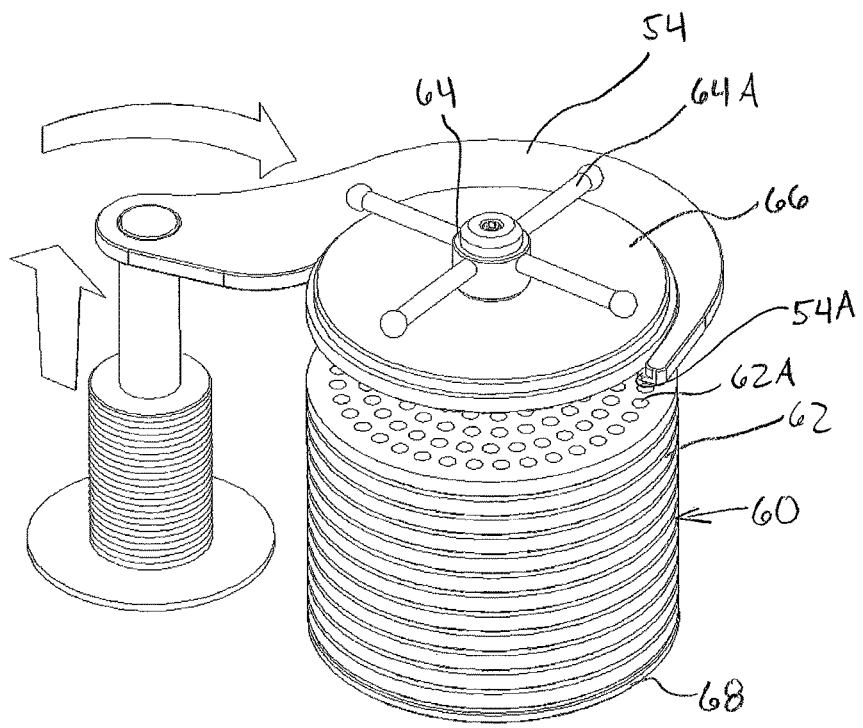
FIG. 9 is a perspective view of a stopper disc stack of a robotic filling system according to some embodiments of the disclosed subject matter.

Referring to FIGS. 6, 8, and 9, once placed on the turntable, the top nut 64 can be rotated to move the top nut 64 from the first, closed position (FIG. 8) to the second, open position (FIG. 9), thereby lifting the top plate 66 and allowing access to the stoppers or other closures within the stopper disc stack 60. In this way, the stoppering arm 50 can gain access to and pick up the stoppers or other closures for placement within the openings of the containers 90, as described above.

In one example, the turntable is rotated to rotate the stopper disc stack 60 while the stoppering arm 50 is stoppering containers 90 to reduce the amount of movement of the stoppering arm 50. That is, by rotating the stopper disc stack 60, an awaiting stopper or other closure can be moved to a position relatively close to location of the stoppering arm 50 within the chamber 20. Also, by rotating the stopper disc stack 60, the number of pick-up or home locations for the stoppering arm 50 can be reduced. That is, one pick-up location can be programmed for each ring of recesses 62A in the discs 62, so that the disc 62 can be rotated to place a recess 62A having a stopper or other closure therein at the pick-up location prior to the stoppering arm 50 picking up a stopper. For instance, the discs 62 shown in FIG. 7 include five generally concentric rings of recesses 62A, so five pick-up locations can be programmed, one pick-up location corresponding to each of the five rings of recesses 62A. Although discs 62 having five rings of recesses 62A are shown and described, it is contemplated that the discs include more or fewer than five rings of recesses, depending on closure size, recess spacing, material requirements, and sterilization requirements, among other things.

In one example, once one ring of stoppers is exhausted, the pick-up location can be moved to another, unexhausted ring of stoppers. In another example, stoppers at the pick-up locations for each of the rings at a particular rotational location of the disc 62 can be picked up before the disc 62 is rotated to place more stoppers in each of the pick-up locations.

Referring to FIGS. 2, 6, and 9, in one example, the filling system 10 includes a disc holder arm 54 to pick up discs 62, for instance, after all the stoppers or other closures have been removed therefrom to expose the stoppers or other closures of the disc 62 below. In one example, the disc holder arm 54 includes a shoulder 54A configured to fit between adjacent discs 62 and abut a bottom surface of the empty disc 62 to lift the disc 62 from the disc 62 below. As portrayed in FIG. 9, the disc holder arm 54, in one example, is rotated into position with the shoulder 54A disposed between two discs 62. The disc holder arm 54 is then lifted toward the top plate 66 to separate the two discs 62 to allow for the stoppering arm 50 to access and pick up stoppers from the disc 62 below. When the stoppers are exhausted from this disc 62, the already-lifted disc 62 can be lowered back down, and the disc holder arm 54 can be repositioned below the newly-exhausted disc 62 and raised to lift the two (or more) empty discs 62 and expose the stoppers of another disc 62 until all of the stoppers of the stopper disc stack 60 are exhausted, at which point the stopper disc stack 60 can be replaced. In other examples, the discs 62 can be raised or lowered by the disc holder arm 54 regardless of whether all of the stoppers are removed from a disc 62. For instance, in one example, the disc holder arm 54 is used to expose another disc 62 holding stoppers of a different size or a different material for containers of different sizes or containers filled with products requiring different closure materials, respectively.

Accordingly, the above-described systems and methods allow for robotic filling of containers. In one example, the system allows for the aseptic filling of vials and syringes, particularly for small and developmental runs of potent and/or toxic materials. In one example, the systems provide an automated aseptic filling system that does not require the use of unique or specialized components for various container sizes. In one example, the system allows for filling of various sized or shaped containers, provided a recognizable container opening exists. Also, the optical system can allow for inspection of containers prior to filling, thus reducing the possibility of rejection due to container defects post-filling. Additionally, pre-fill inspection can be achieved with the optical sensor without the use of additional parts or manual steps. In one example, the systems are configured to be minimally disruptive to sterilized air flows commonly used in aseptic filling.

In this way, in some examples, randomly placed containers can be filled automatically, potentially resulting in labor and time savings. The optical sensor system allows for precision targeting and filling of containers, which can lead to reduced potential for spills of high-value or toxic materials that could require containment. Because the filling system, in some examples, is capable of handling various products and variously sized and shaped containers, the filling system is relatively rapidly adaptable for new products and processes. Also, by using optical sensors in some examples, the system allows for reduction of product losses due to inclusion of a pre-fill inspection of containers. Additionally, because the system is relatively small and contained, the system provides for relatively easy cleaning of surfaces and parts. Moreover, by being configured to accept variously sized and shaped containers, the system allows for reduced cost because little or no container-specific parts are needed.

The above-described systems and methods also allow for robotic stoppering of containers. The discs, in some examples, are configured to allow penetration of sterilant to the closures held by the discs from above and below through the holes and convolutions of the discs. The sandwiched discs of the stopper disc stack can be configured to allow the closures to be sterilized and transferred on multiple axes without movement of the closures within the stopper disc stack. The stopper disc stack can be configured to allow for servo-actuated pick and place handling, for instance using the stoppering arm, as part of the automated filling system. The stopper disc stack also can be configured to allow for automatic actuation for pick and placement of closures. The stopper disc stack can be configured to be transferred through the use of transfer isolators or other such containers using ports, such as rapid transfer ports, to enable aseptic and contained transfers between rooms or barrier isolation systems. In some examples, the discs are configured to accommodate multiple closure types, including lyophilization stoppers, serum stoppers, and syringe stoppers.

In this way, in some examples, the system can allow for the use of robotic filling in a discontinuous manner to produce sterile pharmaceutical products, reducing if not eliminating the need for conveyors, vibrating bowls, handling chutes, or other such closure handling equipment. Additionally, the stopper disc stack allows for reduced manual handling during sterile operations, reducing the likelihood of aseptic interventions in sterile processing. Also, the system allows for multiple stopper disc stacks to be sterilized off-line and made available on a modular basis during filling operations.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system for filling containers with a product, comprising:
    an aseptic controlled environment chamber;
    a filling arm disposed within the chamber; and
    a sensor configured to sense openings of the containers within the chamber, wherein locations of the sensed openings are used to automatically guide the filling arm to fill the containers with product; and
    a stopper disk stack configured to hold stoppers for use in closing openings of the containers, wherein the stopper disc stack is configured to be introduced within the chamber without disrupting the aseptic controlled environment chamber.

2. The system of claim 1 wherein the sensor includes an optical sensor.

3. The system of claim 1 wherein the sensor includes a camera system.

4. The system of claim 1 wherein the sensor includes a laser system.

5. The system of claim 1 further comprising a first controller portion responsive to the sensor to identify locations of openings of the containers, and a second controller portion responsive to the first controller portion and being operative to guide the filling arm to fill the containers.

6. The system of claim 5 wherein the first and second controller portions are part of the same controller.

7. The system of claim 5 wherein the first controller portion includes pattern recognition software.

8. The system of claim 1 wherein the filling arm is an articulated filling arm including at least a first member and a second member joined by an articulation, wherein the second member includes means for filling containers.

9. The system of claim 1 wherein the filling arm includes a servo-driven robotic arm.

10. A system for filling containers with a product, comprising:
    an aseptic controlled environment chamber;
    a filling arm disposed within the chamber; and
    a sensor configured to sense openings of the containers within the chamber, wherein locations of the sensed openings are used to automatically guide the filling arm to fill the containers with product; and
    an articulated holding arm disposed within the chamber including at least a first member and a second member joined by an articulation, wherein the second member includes means for holding a group of containers.

11. The system of claim 10 wherein the articulated holding arm has a range of motion that allows the articulated holding arm to move the means for holding to a plurality of different positions in the chamber.

12. The system of claim 11 wherein the means for holding includes means for holding a tray.

13. The system of claim 12 wherein the sensor is configured to sense openings of the containers disposed in a tray while the tray is being held by the means for holding a tray.

14. The system of claim 10 wherein the articulated holding arm includes a robotic apparatus.

15. The system of claim 10 further comprising a controller for operating the articulated holding arm in response to the sensor.

16. The system of claim 8 wherein the articulated filling arm has a range of motion that allows the articulated holding arm to move the means for filling to fill the containers within the chamber.

17. The system of claim 10 wherein the articulated holding arm includes a servo-driven robotic arm.

18. The system of claim 10 wherein the sensor includes an optical sensor.

19. The system of claim 10 wherein the sensor includes a camera system.

20. The system of claim 10 wherein the sensor includes a laser system.

21. The system of claim 10 further comprising a first controller portion responsive to the sensor to identify locations of openings of the containers, and a second controller portion responsive to the first controller portion and being operative to guide the filling arm to fill the containers.

22. The system of claim 21 wherein the first and second controller portions are part of the same controller.

23. The system of claim 21 wherein the first controller portion includes pattern recognition software.

24. The system of claim 10 wherein the filling arm is an articulated filling arm including at least a first member and a second member joined by an articulation, wherein the second member includes means for filling containers.

25. The system of claim 24 wherein the articulated filling arm has a range of motion that allows the articulated holding arm to move the means for filling to fill the containers within the chamber.

26. The system of claim 10 wherein the filling arm includes a servo-driven robotic arm.

* * * * *

UNITED STATES PATENT AND TRADEMARK OFFICE
CERTIFICATE OF CORRECTION

PATENT NO. : 10,261,940 B2  
APPLICATION NO. : 15/680114  
DATED : April 16, 2019  
INVENTOR(S) : Christopher A. Procyshyn et al.

Page 1 of 1

It is certified that error appears in the above-identified patent and that said Letters Patent is hereby corrected as shown below:

In the Claims

Column 11, Claim 16, Line 9 "The system of claim 8" should read --The system of claim 15--.

Signed and Sealed this  
Fifth Day of April, 2022

Drew Hirshfeld  
*Performing the Functions and Duties of the*  
*Under Secretary of Commerce for Intellectual Property and*  
*Director of the United States Patent and Trademark Office*